(12) United States Patent
Zou et al.

(10) Patent No.: US 6,186,649 B1
(45) Date of Patent: Feb. 13, 2001

(54) LINEAR ILLUMINATION SOURCES AND SYSTEMS

(75) Inventors: Han Zou, Windsor; Scott M. Zimmerman, Basking Ridge; John Colvin Wilson, Wayne; Karl W. Beeson, Princeton; Michael James McFarland, Washington, all of NJ (US); Hefen Lin, Cupertino, CA (US); Jerry Wayne Kuper, Martinsville; Lawrence Wayne Shacklette, Maplewood, both of NJ (US)

(73) Assignee: Honeywell International Inc., Morristown, NJ (US)

( * ) Notice: Under 35 U.S.C. 154(b), the term of this patent shall be extended for 0 days.

(21) Appl. No.: 09/061,562

(22) Filed: Apr. 16, 1998

(51) Int. Cl.[7] ........................................................ F21V 7/00
(52) U.S. Cl. ............................ 362/347; 362/217; 362/296
(58) Field of Search ............................ 362/217, 219, 362/225, 296, 298, 341, 347, 260, 259, 800

(56) References Cited

U.S. PATENT DOCUMENTS

| | | | |
|---|---|---|---|
| 4,074,124 | * | 2/1978 | Maute et al. ........................ 362/217 |
| 4,169,675 | | 10/1979 | Roberts ............................... 355/85 |
| 4,367,518 | | 1/1983 | Roberts ............................... 362/224 |
| 4,521,835 | * | 6/1985 | Meggs et al. ........................ 362/217 X |
| 4,597,034 | * | 6/1986 | Kendall-Tobias ..................... 362/217 |
| 4,941,072 | | 7/1990 | Yasumoto ............................ 362/249 |
| 5,036,436 | * | 7/1991 | Rattigan et al. ..................... 362/217 X |
| 5,103,385 | | 4/1992 | Federico et al. ..................... 362/298 |
| 5,241,459 | | 8/1993 | Kaplan et al. ....................... 362/298 |
| 5,276,600 | * | 1/1994 | Takase et al. ....................... 362/341 X |
| 5,453,849 | | 9/1995 | Copenhaver et al. ................. 358/475 |
| 5,523,655 | | 6/1996 | Jennato et al. ...................... 315/246 |
| 5,565,958 | | 10/1996 | Kaplan ................................ 355/67 |

FOREIGN PATENT DOCUMENTS

| | | | |
|---|---|---|---|
| 2 255 551 | 7/1975 | (FR) | ................................ F21V/7/00 |
| 1 533 870 | 11/1978 | (GB) | ............................... G03G/15/04 |
| 2 020 000 | 11/1979 | (GB) | ................................ F21V/7/12 |

OTHER PUBLICATIONS

PCT Search Report.
English Abstract 2 255 551 A.

* cited by examiner

Primary Examiner—Laura K. Tso
(74) Attorney, Agent, or Firm—John G. Shudy, Jr.

(57) ABSTRACT

Improved linear illumination sources are disclosed which utilize external, highly reflective enclosures containing one or more linear openings and thereby achieve improved source efficiency, output irradiance and/or output radiance. Such improved illumination sources may be combined with additional optical elements to produce more complex illumination systems.

23 Claims, 13 Drawing Sheets

LINEAR ILLUMINATION SOURCES AND SYSTEMS

BACKGROUND OF THE INVENTION

1. Field of Invention

The present invention generally relates to high-efficiency, linear illumination sources and linear illumination systems which have enhanced output irradiance and radiance. Irradiance is defined as the light flux per unit area and can be expressed, for example, in units of watts per square centimeter ($W/cm^2$). Radiance is the brightness of the light. Radiance can be expressed, for example, in units of watts per square centimeter per steradian ($W/(cm^2 \cdot steradian)$), where a steradian is the unit of solid angle.

For many applications, an illumination source with a narrow output opening and high output efficiency is preferred. Such a source is commonly constructed using an aperture lamp with an internal slit aperture built into the lamp structure. However, an aperture lamp generally has lower light emission than a conventional lamp due to increased light absorption inside the lamp and due to a reduction in the surface area of the phosphor coating. It would be highly desirable to have an improved narrow illumination source that is more efficient than a lamp with an internal slit aperture.

For applications such as, for example, optical scanners and photocopiers, a linear illumination system with high output irradiance is desired in order to illuminate a narrow strip of the area being scanned or photocopied. The illumination assembly for such a device commonly consists of a bare linear light source, an aperture lamp, or a lamp partially surrounded with a specular reflector. A specular reflector is a mirror-like reflector with a smooth surface and has the property that the angle of light incidence equals the angle of reflection, where the incident and reflection angles are measured relative to the direction normal to the surface. An improved linear illumination system which has higher output irradiance would be advantageous.

For certain other applications such as flat panel displays, an illumination system having a very shallow thickness is highly desirable. Such systems are commonly configured with one or more illumination sources, a waveguide or light pipe for collecting and distributing the light from the illumination sources, and additional scattering, reflecting, or collimating elements for extracting the light from the waveguide. A significant depth savings can be achieved by coupling the illumination sources through the edge of the waveguide. The amount of light extracted from the system is proportional to the number of reflections or scattering events that occur within the waveguide, the number being inversely proportional to the thickness of the waveguide. To obtain maximum light output, a thin waveguide is preferable. However, this results in waveguide edges having a small surface area, limiting the size of the illumination source that can directly adjoin the edge of the waveguide. On the other hand, if the surface area of the waveguide edge is increased, the extraction efficiency of the waveguide will decrease. It would be highly desirable to utilize a thin waveguide yet provide the maximum illumination source input. Therefore, a highly-efficient, linear illumination source with high output irradiance and radiance from a narrow opening is needed.

2. Description of the Prior Art

It is well-known that it is possible to use tubular fluorescent lamps having an internal slit aperture in order to concentrate and direct the emitted light into a narrow angular range. Two types of aperture lamps with internal slits are in general use. The first type is shown in cross section as aperture lamp 10 in FIG. 1. The lamp is composed of a hollow glass tube 12 having a phosphor coating 14 on the entire inside surface except in one narrow region 16 subtending angle 18. The center of the tube is filled with a mixture of gases which, when excited by an electric current supplied by electrodes (not shown) at the ends of the tube, emits ultraviolet light. The ultraviolet light, in turn, strikes the phosphor coating 14 and is converted to visible light. A typical phosphor coating is also a diffuse reflector. Note that a diffuse reflector is a reflector that scatters incident light into a range of angles. Diffuse reflectors typically have high reflectivity only when the reflective coating is relatively thick (e.g. about 0.15 mm or greater). The reflective phosphor coating on the inside of an aperture lamp is, by necessity, significantly thinner than 0.15 mm resulting in poor reflectivity (on the order of 60–80%). Most of the light not reflected by the phosphor is transmitted through the coating. By placing an aperture, in this case gap 16, in the phosphor coating, light can be directed preferentially out the aperture. However, due to loss of some of the light through the phosphor coating, the effectiveness of this type of aperture lamp is significantly reduced.

A second type of lamp having an internal aperture and known to those skilled in the art is shown in FIG. 2 as aperture lamp 50. The lamp has a glass tube 52. Inside the glass tube is a phosphor coating 54 and an additional reflective coating 56. There is an aperture opening 58 through both the phosphor coating 54 and reflective coating 56 which subtends angle 59 and which allows light to escape preferentially in one direction.

There are six significant problems associated with the internal aperture lamps 10 and 50 shown in FIGS. 1 and 2. First, the phosphor and reflective coatings must be very thin and the selection of coating materials is very limited so as not to interfere with the operation of the lamp. No organic materials are possible for an internal coating because any outgassing from the organic material or decomposition of the organic material from the effects of ultraviolet light would lower the efficiency of the lamp. Second, because of the restrictions on coating materials, the reflectivity of the coatings is not as high as desired. Third, a significant amount of ultraviolet light generated inside the lamp is wasted due to absorption by the glass tube in the area without the phosphor coating. Fourth, a more expensive glass must be used to make these types of aperture lamps in order to reduce ultraviolet light induced discoloration and loss of light transmission of the glass in the area of the aperture. Fifth, because the area of the internal lamp surface which is covered by the phosphor coating is reduced by the area which includes the aperture, there is a corresponding reduction in the efficiency of converting electrical power to light energy. Sixth, internal aperture lamps are more difficult to manufacture than conventional lamps and therefore are more expensive. Such deficiencies contribute to reduced efficiency and higher costs for aperture lamps compared to regular lamps without internal apertures.

Accordingly, there are now provided with this invention improved linear illumination sources which utilize external, highly reflective enclosures incorporating one or more linear openings in order to achieve improved source efficiency, output irradiance and output radiance. Such improved illumination sources may be combined with additional optical elements to produce more complex illumination systems. Additional objects of the present invention will become apparent from the following description.

SUMMARY OF THE INVENTION

One embodiment of the present invention is an improved linear illumination source. The linear illumination source comprises: (a) a linear light source having a width w, in a direction perpendicular to the long axis of the linear source, and (b) a external reflective enclosure partially surrounding the aforementioned linear light source, wherein the external reflective enclosure has a maximum inside width $w_2$, and wherein the external reflective enclosure has at least one linear opening of maximum width $w_3$ such that $(0.03)(w_2) \leq w_3 \leq (0.75)(w_2)$. A linear light source is defined as a light source having a length dimension that is at least three times the width dimension $w_1$. A linear light source may be comprised of a single element or may be a linear array containing a multiplicity of elements. If the linear light source is an array containing a multiplicity of elements, then the length of the array is at least three times the width of an individual element. A linear opening is defined as an opening having a length dimension that is at least three times the width dimension.

Another embodiment of the invention is disclosed which is directed to a linear illumination system which utilizes the aforementioned linear illumination source and one or more additional optical elements in order to achieve a system with high optical efficiency and high output irradiance and/or radiance. Such a linear illumination system comprises: (a) a linear light source having a width $w_1$ in a direction perpendicular to the long axis of the linear source, (b) an external reflective enclosure partially surrounding the aforementioned linear light source, wherein the external reflective enclosure has a maximum inside width $w_2$, and wherein the external reflective enclosure has at least one linear opening of maximum width $w_3$ such that $(0.03)(w_2) \leq w_3 \leq (0.75)(w_2)$, and (c) at least one optical element in close proximity to at least one linear opening. An optical element may include, for example, a cylindrical rod lens, a lenticular lens, an aspherical lenticular lens, a lenticular prism, an array of lenticular lenses, an array of lenticular prisms, a mirror, a reflecting concentrator, or a waveguide. By lenticular, we mean a linear optical element having the cross-section (in one direction only) of a lens or a prism.

The embodiments of the present invention will be better understood by reference to the following detailed discussions of specific embodiments and the attached figures which illustrate and exemplify such embodiments.

BRIEF DESCRIPTION OF DRAWINGS

The invention will be more fully understood and further advantages will become apparent when reference is made to the following detailed description of the invention and the accompanying drawings in which.

DESCRIPTION OF THE INVENTION

The following preferred embodiments as exemplified by the drawings are illustrative of the invention and are not intended to limit the scope of the invention as encompassed by the claims of this application. Illumination sources and illumination systems using improved external reflective enclosures, linear openings and, optionally, additional optical elements are disclosed herein.

Figure 3:
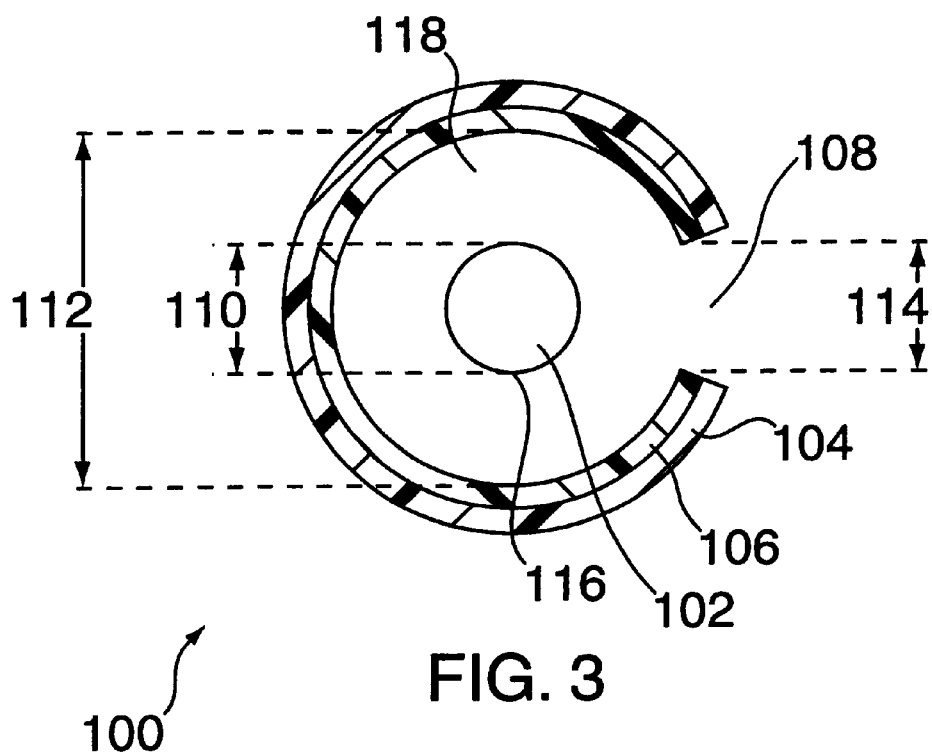
FIG. 3 is a schematic cross-sectional diagram of a linear illumination source.

One embodiment of this invention is a linear illumination source 100 shown in cross-section in FIG. 3. Linear illumination source 100 is comprised of linear light source 102 that is partially surrounded by an external enclosure 104. The linear light source 102 may be centered in the external enclosure 104 or displaced to one side of the enclosure. One or more linear openings 108 in the wall of the external enclosure allow light to escape from the enclosure. In close proximity to the inside surface of the external enclosure 104 is a reflective layer 106. In this figure, the width of the linear light source is 110, the maximum inside width of the external enclosure is 112, and the maximum width of the linear opening is 114. Optionally, if the external enclosure 104 is constructed from a transparent material, the external enclosure may completely surround the linear light source 102. However, an opening 108 must still remain in the reflective layer 106 in order for light to escape from the linear illumination source.

The linear light source 102 can be any source that emits light. Exemplary linear light sources include, but are not limited to, one or more of the following types of light sources: fluorescent lamps, light emitting diodes (LEDs), laser diodes, organic light emitting diodes, electroluminescent strips, or high-intensity discharge lamps. As an illustrative example, a multiplicity of light emitting diodes placed in a row is a linear light source. The single or multiple elements of the linear light source may emit light of one color, multiple colors, or white light (which is composed of multiple colors). The linear light source 102 illustrated in FIG. 3 can emit light in all directions. A fluorescent lamp is an example of a linear light source 102 that emits light in all directions. In order to maximize the efficiency of the linear illumination system 100, it is preferable that linear light source 102 have a non-absorptive surface 116. Such a non-absorptive surface 116 may be reflective, transmissive or both.

There is a gap 118 between the surface 116 of the linear light source 102 and the reflective layer 106. Having a gap between linear light source 102 and the reflective layer 106 is critical if the linear light source 102 is a fluorescent lamp or other type of lamp where the magnitude of the light output of the lamp is sensitive to the lamp temperature. The gap 118 can act as an insulating layer which will allow the linear light source 102 to warm up quickly to its optimum operating temperature. Preferably the gap is greater than about 10% of the width 110 of the linear light source.

The external enclosure 104 shown in FIG. 3 can have any cross-sectional shape including, but not limited to, circular, elliptical, oval, cusp-shaped, or faceted. The linear opening 108 preferably has a maximum width 114 that is less than the maximum inside width 112 of the external enclosure 104. More preferably, the maximum width 114 of linear opening 108 ranges from about 3% to about 75% of the maximum inside width 112 of the external enclosure. Most preferably, the maximum width 114 of linear opening 108 ranges from about 5% to about 50% of the maximum inside width 112 of the external enclosure. In addition, if linear light source 102 is a tubular fluorescent lamp, preferably the maximum width 114 of linear opening 108 ranges from about 10% to about 100% of the width 110 of the linear light source. More preferably, the width 114 of the linear opening 108 ranges from about 20% to about 90% of the width 110 of the linear light source. The width of the linear opening 108 may be uniform along the length of the linear light source or the width of linear opening 108 may vary along the length of the linear light source in order to change the output light distribution along the light source. This latter feature of the current invention provides a critical advantage for applications requiring a uniform illumination, whereby the non-uniformity inherent in the light output of the lamp can be corrected to give a uniform irradiance. The width of the aperture can be widened at any point along the length of the lamp where the lamp output is low in order to provide a relatively constant and uniform output from the illumination source.

The reflective layer 106 may be constructed from any material that reflects light. The reflective layer may be a diffuse reflector, a specular reflector, or a combination of specular and diffuse reflectors.

Figure 4:
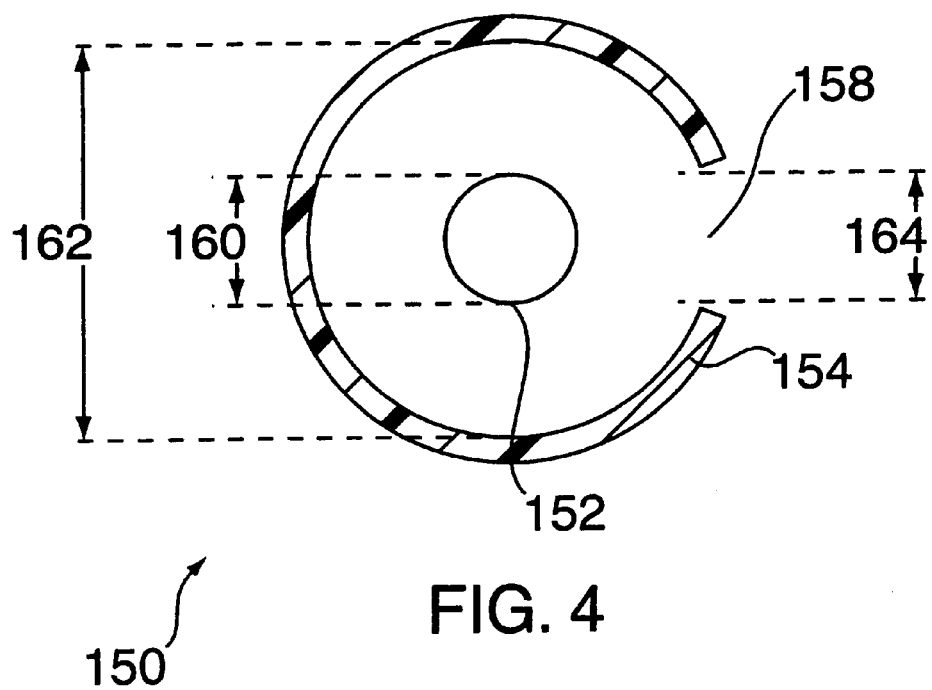
FIGS. 4 and 5 are respectively, schematic cross-sectional and perspective diagrams of an alternative version of a linear illumination source.
Figure 5:
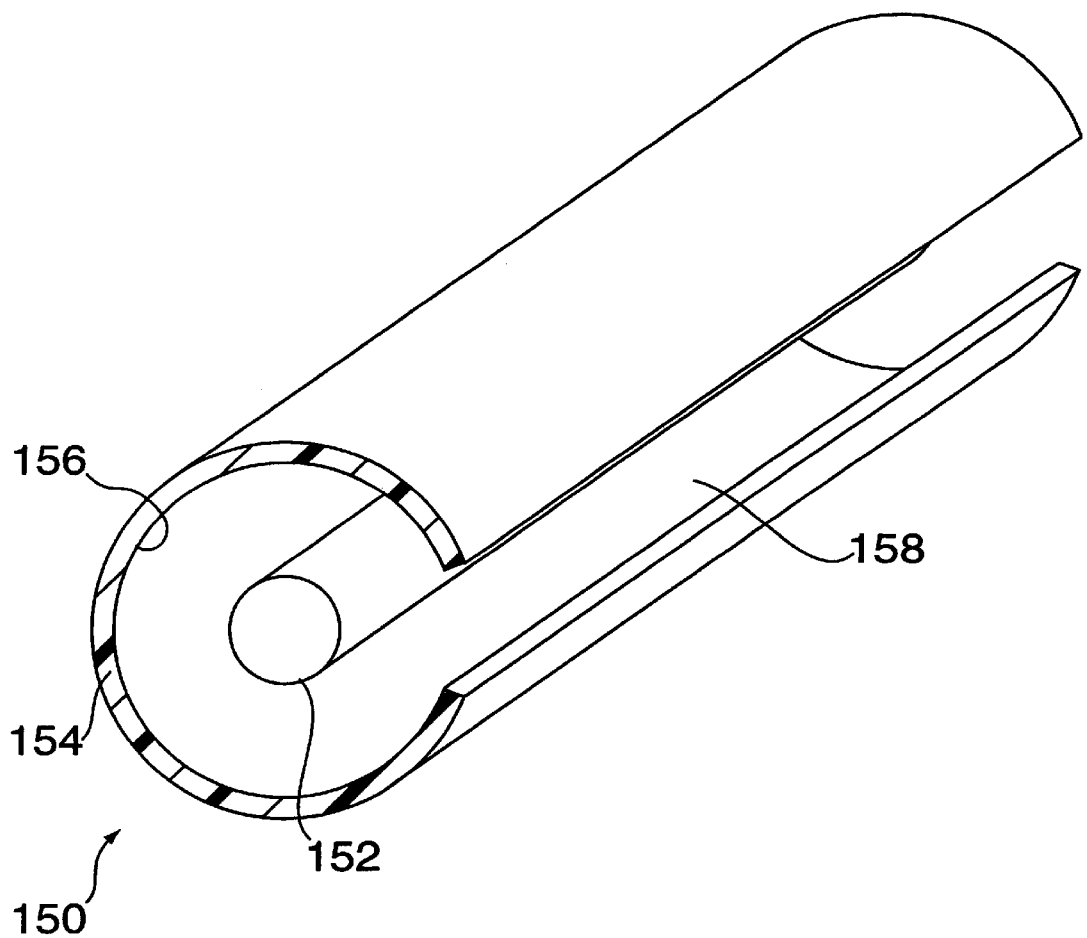

Diffuse reflectors can be made that have very high reflectivities (for example, greater than 95% or greater than 98%). However, diffuse reflectors with high reflectivities are generally quite thick. For example, diffuse reflectors with reflectivities greater than 98% are typically several millimeters thick. Examples of diffuse reflectors include, but are not limited to, fluoropolymer materials such as Spectralon™ from Labsphere, Inc. and polytetrafluoroethylene ) film from Fluorglas (sold under the trade name Furon™), W. L. Gore and Associates, Inc. (sold under the trade name DR™), or E. I. du Pont de Nemours & Company (sold under the trade name of Teflon™), films of barium sulfate, porous polymer films containing tiny air channels such as polyethersulfone and polypropylene filter materials made by Pall Gelman Sciences, and polymer composites utilizing reflective filler materials such as, for example, titanium dioxide. An example of the latter material is titanium-dioxide-filled ABS (acrylonitrile-butadiene-styrene terpolymer) produced by RTP. In the case that a structural material is employed as a reflective material, such as titanium dioxide filled ABS, the structural support 104 can be combined with the reflective layer 106 as shown in FIGS. 4 and 5.

Most specular reflective materials have reflectivities ranging from about 80% to about 93%. Any light that is not reflected by the specular reflector is absorbed and converted to heat, thus lowering the efficiency of any optical system utilizing such a reflector. Examples of specular reflective materials include, but are not limited to, Silverlux™, a product of 3M, and other carrier films of plastic which have been coated with a thin metallic layer such as silver, aluminum or gold. The thickness of the metallic coating may range from about 0.05 $\mu$m to about 0.1 mm, depending on the materials used and the method of manufacturing the metal coating.

An example of a combination of specular and diffuse reflective materials is one or more layers of a diffuse reflector that is backed by a specular reflector. Such a combination of specular and diffuse reflective materials is disclosed in U.S. patent application Ser. No. 08/679,047 and is incorporated herein by reference. The use of a combination of specular and diffuse reflective materials may result in higher reflectivity in a thinner layer than is possible using a diffuse reflective material alone.

The efficiency of illumination source 100 can be defined as the percentage of the light emitted from linear light source 102 that escapes through linear opening 108. The efficiency depends strongly on the width 114 of linear opening 108, the circumference of the inside surface of reflective layer 106, the reflectivity of the reflective layer 106 and the reflectivity of the linear light source 102. For example, if the width 114 of linear opening 108 is $\frac{1}{10}$ of the circumference of the inside surface of reflective layer 106, then only 10% of the light that is emitted from linear light source 102 will escape through linear opening 108 without being reflected by reflective layer 106. The remaining 90% of the light will be reflected one or more times by reflective layer 106 or by the linear light source 102 before escaping from linear opening 108 or before being absorbed by the reflective surfaces and converted to heat. Some of the light may be reflected ten times or more before escaping. The large number of times that the light can be reflected makes it very important that the reflectivity of the reflecting layer 106 be as close to 100% as the practical considerations of space and cost will allow. For example, if the reflectivity of an optical surface is 90% per reflection and the light reflects ten times from that surface, the overall efficiency is $(0.90)^{10}$ or 35%. The other 65% of the light is lost. However, if the reflectivity of the reflector is increased to 95% per reflection and the light reflects ten times from that surface, the overall efficiency is $(0.95)^{10}$ or 60%, a significant improvement over 35%. Greater improvements may be attained if the reflectivity is greater than 95%. Thus, for the present invention, the reflectivity of the material employed for layer 106 is preferably greater than 90%, more preferably greater than 95%, and most preferably greater than about 97%.

Figure 19:
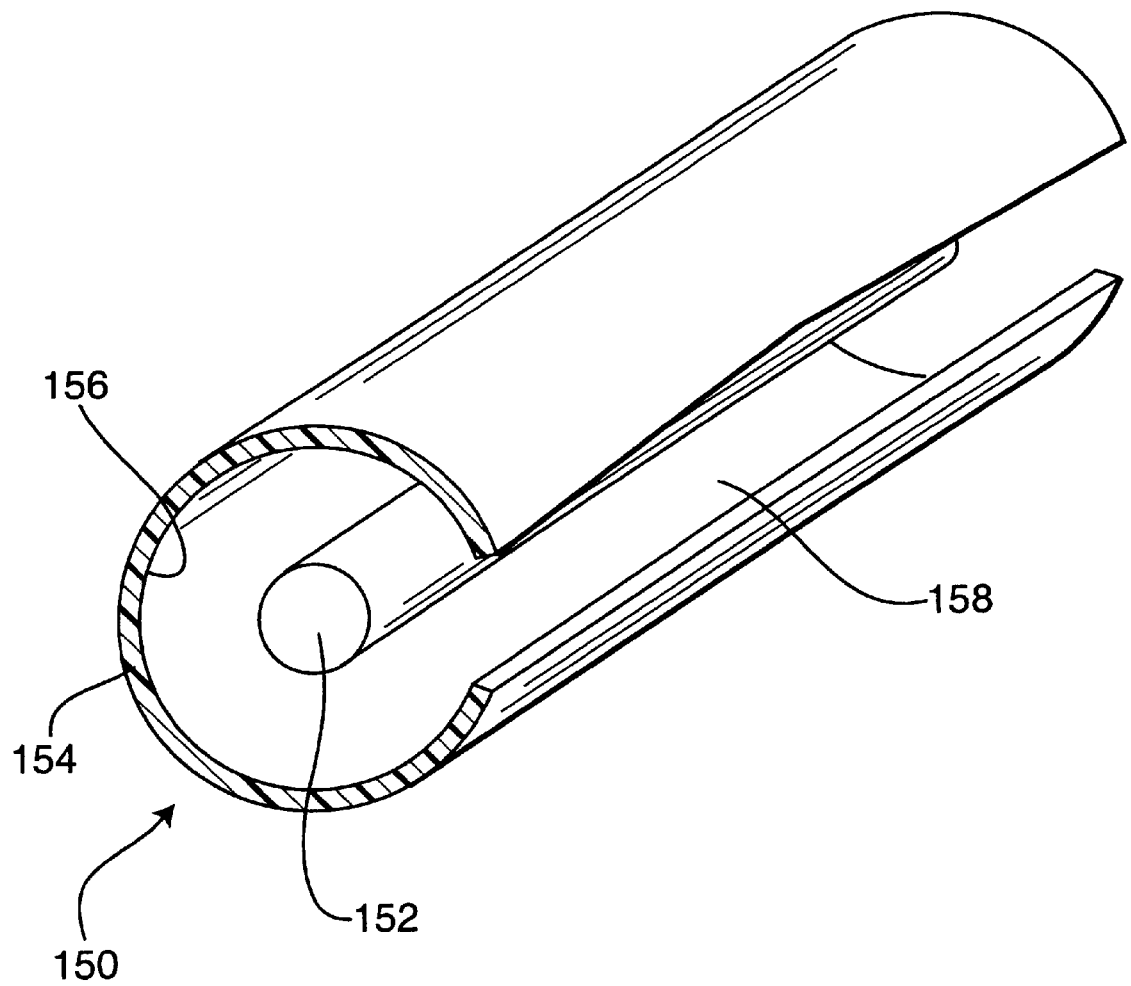
FIG. 19 shows a linear opening which varies in width along the length of the illumination source.

Another embodiment of this invention is shown as linear illumination source 150 in FIG. 4 (a cross-sectional view) and in FIG. 5 (a perspective view). In this embodiment, linear light source 152 having width 160 is partially surrounded by an external reflective enclosure 154 having a maximum inside width 162. One or more linear openings 158 in the wall of the external reflective enclosure 154 allow light to escape from the enclosure. The maximum width of the linear opening 158 is dimension 164. The external reflective enclosure 154 shown in FIGS. 4 and 5 can have any cross-sectional shape including, but not limited to, circular, elliptical, oval, cusp-shaped, or faceted. The linear opening 158 preferably has a maximum width 164 that is less than the maximum inside width 162 of the external reflective enclosure 154. More preferably, the maximum width 164 of linear opening 158 ranges from about 3% to about 75% of the maximum inside width 162 of the external reflective enclosure. Most preferably, the maximum width 164 of linear opening 158 ranges from about 5% to about 50% of the maximum inside width 162 of the external reflective enclosure. In addition, if linear light source 152 is a tubular fluorescent lamp, preferably the maximum width 164 of linear opening 158 ranges from about 10% to about 100% of the width 160 of the linear light source. More preferably, the width 164 of the linear opening 158 ranges from about 20% to about 90% of the width 160 of the linear light source. The width of the linear opening 158 may be uniform along the length of the linear light source or the width of linear opening 158 may vary along the length of the linear light source in order to change the output light distribution along the light source to compensate for non-uniformities in the light source as shown in FIG. 19.

The embodiment shown in FIGS. 4 and 5 is similar to FIG. 3 except that now the structural material of the external enclosure 154 is also the reflective material. This embodiment is especially useful if the structural material for the external reflective enclosure is a diffuse reflector. Examples of diffuse reflectors are listed above. Preferably the reflective material can be cut, formed, extruded, or molded into the required shape for the external reflective enclosure and, of course, possesses sufficient tensile modulus, flexual modulus, heat deflection temperature, and impact resistance to serve as the structural member for the illumination system.

Preferred reflective materials for use in the particular embodiments 150, 200, 300, 350, 400, 450, and 500 are engineering thermoplastics which have been filled with fine particles which have an index of refraction which is substantially greater than that of the host polymer and are optically clear or white in their neat form, such as titanium dioxide (rutile and anatase), aluminum oxide, zinc oxide, zinc sulfide, barium sulfate, antimony oxide, magnesium oxide, calcium carbonate, strontium titantate, and the like. Preferred materials also include engineering thermoplastics which contain particles, voids or gas-filled bubbles created, for example, by foaming, and whereby the particles, voids or bubbles possess an index of refraction substantially less than that of the host polymer. Although the primary particle size can be much finer, as dispersed in the polymer matrix, the filler particles or voids preferably lie in the size range from about 0.1 microns to about 3.0 microns and most preferably from about 0.1 microns to about 1 microns. The optimal size of a filler particle may be predicted from the relation $d=2\lambda°/(\pi n \delta)$, where d is the diameter of the particle, $\lambda°$ is the vacuum wavelength of interest, n is the index of refraction of the matrix polymer and $\delta$ is the difference in the indices of refraction of the filler and the matrix. Thermoplastics useful in this invention are preferably non-yellow and include a wide variety of plastics known in the art to be useful for injection molding or extrusion, such as, for example, ABS, poly (methyl methacrylate) poly(ethylene terephthalate) (PEI), poly(butylene terephthalate) (PBT) polypropylene, nylon 6, nylon 66, polycarbonate, polystyrene, poly(phenylene oxide), and blends and alloys thereof.

Figure 6:
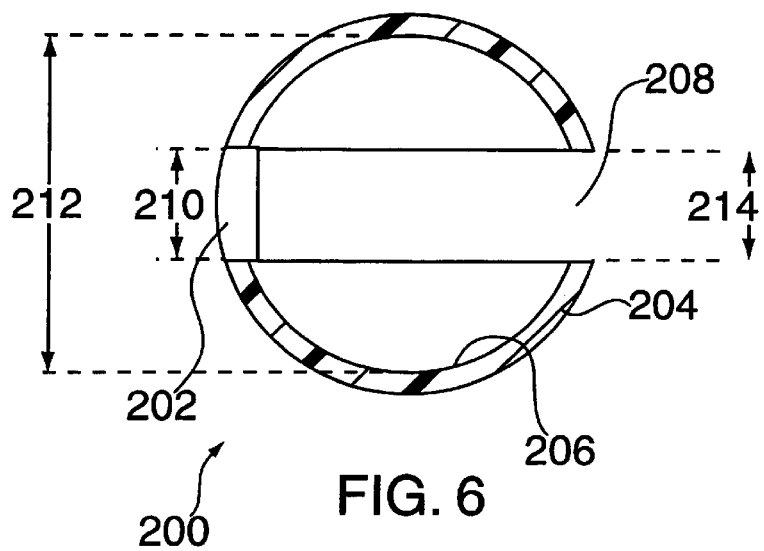
FIGS. 6 and 7 are respectively, schematic cross-sectional and perspective diagrams of another version of a linear illumination source.
Figure 7:
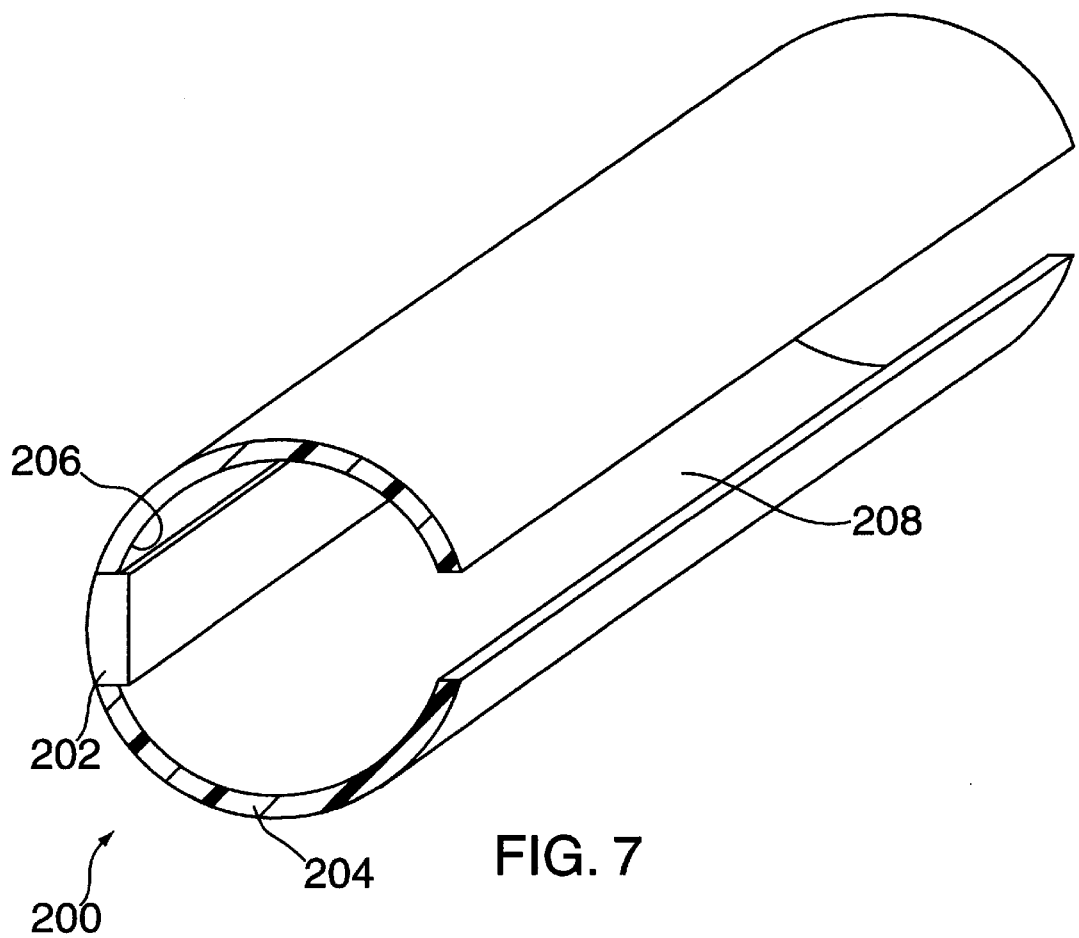

Another embodiment of this invention is shown as linear illumination source 200 in FIG. 6 (a cross-sectional view) and FIG. 7 (a perspective view). In this embodiment, the linear light source 202 having width 210 is embedded into the side of the external reflective enclosure 204 which has a maximum inside width 212. One or more linear openings 208 in the wall of the external reflective enclosure 204 allow light to escape from the enclosure. The maximum width of each linear opening 208 is dimension 214. In FIGS. 6 and 7, the linear opening 208 is illustrated to be on the side of the external reflective enclosure 204 opposite the linear light source 202. However, this is not required and the linear light source 202 and the linear opening 208 may be adjacent to each other. The external reflective enclosure 204 may be constructed from a diffuse reflective material or an additional reflective layer may be placed on the inner surface 206 of external reflective enclosure 204 in order to achieve high reflectivity. The linear light source 202 illustrated in FIGS. 6 and 7 preferably emits light into a hemisphere (a solid angle of $2\pi$) or into a solid angle less than $2\pi$ and preferably does not emit light in all directions (which would be a solid angle of $4\pi$). Examples of linear light source 202 include, but are not limited to, light emitting diodes, laser diodes, organic light emitting diodes, and electroluminescent strips. In this embodiment of the invention, the external reflective enclosure 204 can also serve to homogenize the light output from the linear light source 202. This homogenization is especially important if the linear light source 202 is an array of light emitting diodes, laser diodes, or organic light emitting diodes, each of which may have a very small light emitting surface. If the linear light source 202 includes elements that emit different colors (for example, red, green and blue light emitting diodes), the external reflective enclosure 204 can mix the colors to form a white light output.

Figure 8:
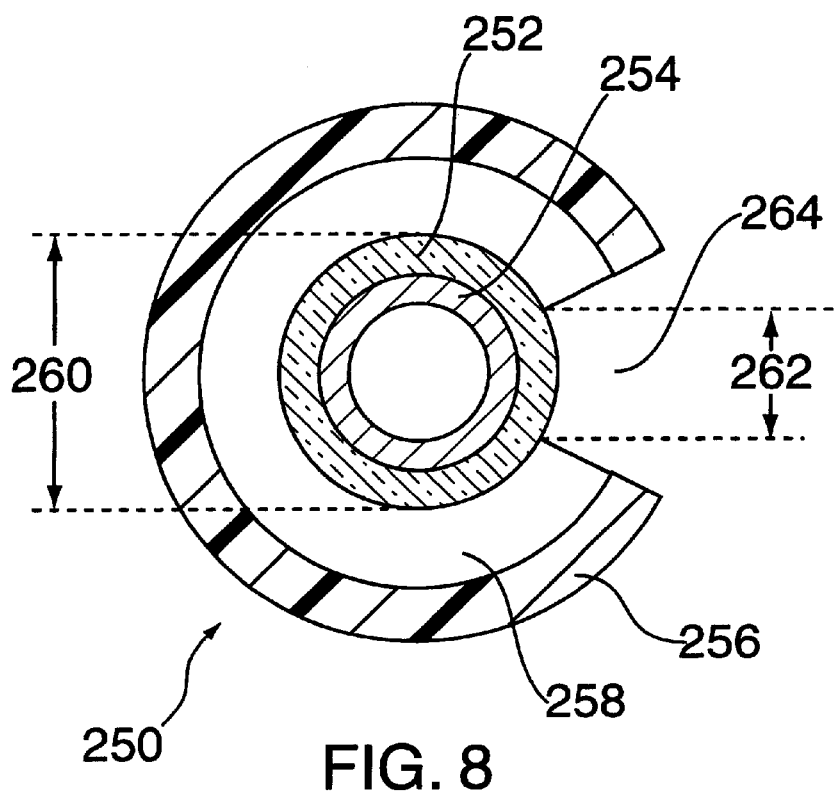
FIG. 8 is a schematic cross-sectional diagram of another linear illumination source.

Another embodiment of this invention is illustrated by the linear illumination source 250 shown in cross-section in FIG. 8. This configuration is especially useful if the linear light source is, for example, a tubular fluorescent lamp which is illustrated in FIG. 8 as a transparent glass envelope 252 that is coated on the inside with a phosphor layer 254. The linear light source is surrounded by external enclosure 256 except for opening 264 having an opening width 262. The external enclosure 256 may be constructed from a reflective material, a non-reflective material, or a transparent material. If the external enclosure is constructed from a non-reflective or transparent material, an additional reflective layer 258 is needed on the inside surface of external enclosure 256. The reflective structure or structures, including external enclosure 256 and/or reflecting layer 258, may be constructed from diffuse reflective materials, specular reflective materials, or a combination of diffuse reflective materials and specular reflective materials. Examples of diffuse and specular reflective materials are listed above. FIG. 8 is similar to FIG. 3 except that in FIG. 8 there is little or no gap between the linear light source and the reflecting layer 258. In the preferred embodiment, the gap is less than 10% of the lamp width 260. If the linear light source is a fluorescent lamp, removing the gap can lead to higher output efficiency of the linear illumination source by decreasing the number of times the light must reflect inside the external reflective enclosure before is escapes from opening 264. (Note that the phosphor coating inside a fluorescent lamp typically has a reflectivity of approximately 60–80% with most of the remainder of the light being transmitted so that it is possible for light to travel from one side of the lamp to the other by passing through the phosphor coating.) However, fluorescent lamps are very sensitive to the temperature of their surroundings. Placing the external enclosure 256 and/or the reflective layer 258 in close proximity or actual contact with the fluorescent lamp may lengthen the warm-up time of the lamp with resulting reduced light output while the lamp is warming up, or may lower the steady-state operating temperature of the fluorescent lamp which again could result in lower light output. Optionally, if the external enclosure 256 is constructed from a transparent material and a reflective layer 258 is utilized, the external enclosure 256 may completely surround the glass envelope 252 of the fluorescent lamp. However, an opening 264 must still remain in reflective layer 258 in order for light to escape from the linear illumination source. An example of the optional configuration would be to use a flexible, diffuse, reflective layer 258 having an opening 264 and to use transparent shrink tubing for the external enclosure 256. After the pieces are assembled into the correct configuration, the shrink tubing can be heated causing it to shrink tightly around the reflector and fluorescent lamp.

Other embodiments of this invention involve using linear illumination sources of the type illustrated in FIGS. 3–8 to make more complex linear illumination systems. The linear illumination systems may include additional optical elements such as, for example, waveguides, cylindrical rod lenses, lenticular lenses, aspherical lenticular lenses, arrays of lenticular lenses, prisms, arrays of lenticular prisms, reflectors, concentrators and collimators. The optical elements may be used to shape, focus, collimate, or project the light being emitted from the linear illumination source. Examples of such illumination systems are illustrated in FIGS. 9–14 and are not meant to limit the scope of this invention. Note, for example, that any of the linear illumination sources illustrated in FIGS. 3–8 may be used with any of the optical elements in order to make additional linear illumination systems. Likewise, the additional optical elements may also be used in combination, such as the lens of FIG. 10 together with the light guide of FIG. 9, or a lens and CPC can be integrated together, or multi-stage CPC's in series may be employed.

Figure 9:
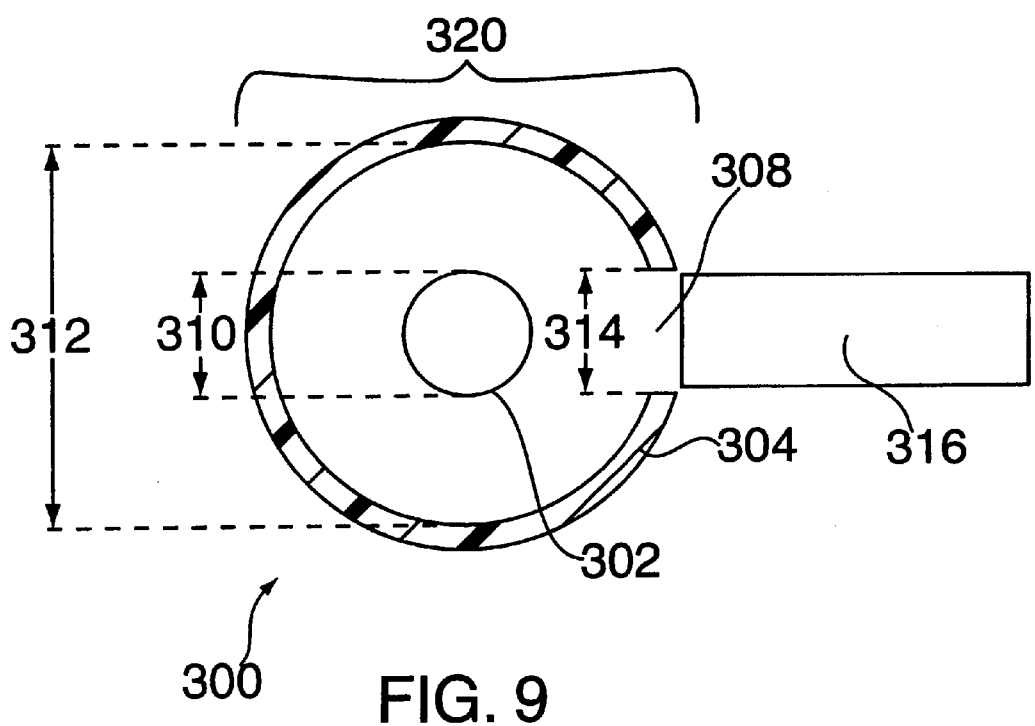
FIG. 9 is a schematic cross-sectional diagram of a linear illumination system utilizing the linear illumination source of FIG. 4 and a waveguide.

The diagram in FIG. 9 illustrates another embodiment of this invention. Linear illumination system 300 is comprised of a linear illumination source 320 and optical waveguide 316. By way of example, linear illumination source 320 is illustrated to be of the type shown previously in FIG. 4 and is further comprised of a linear light source 302 and a external reflective enclosure 304. A linear opening 308 in external reflective enclosure 304 allows light to pass from the linear illumination source 320 to an optical waveguide 316. The optical waveguide may be used to transport the light by total internal reflection (TIR) to places remote from the linear illumination source 320. As will be understood by those skilled in the art, other optical components may be used with optical waveguide 316 to form additional illumination systems. Applications for such linear illumination systems include edge-lit illumination systems for flat panel displays and collimating illumination systems.

Figure 10:
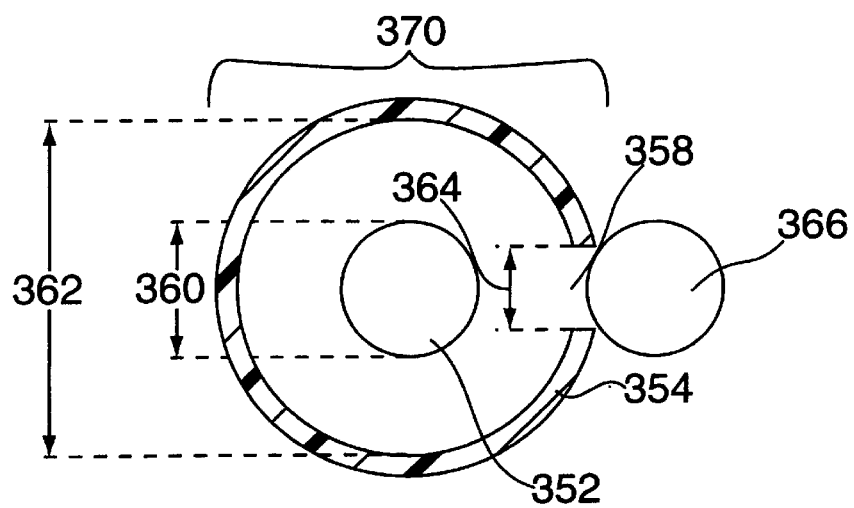
FIGS. 10 and 11 are, respectively, schematic cross-sectional and perspective diagrams of a linear illumination system utilizing the linear illumination source of FIG. 4 and a lens.
Figure 11:
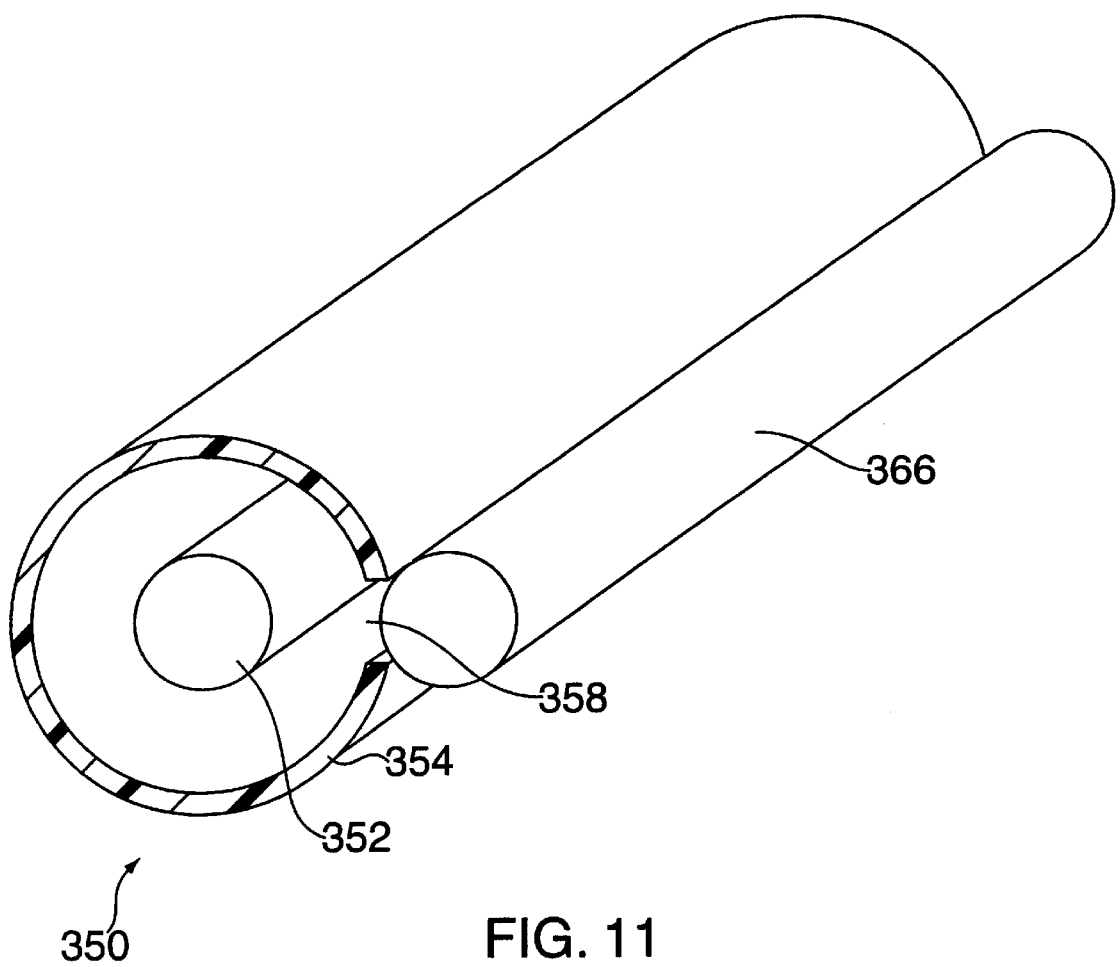

Illustrated in FIG. 10 (a cross-sectional view) and FIG. 11 (a perspective view) is another embodiment of this invention. Linear illumination system 350 is comprised of linear illumination source 370 and a lens 366. By way of example, linear illumination source 370 is illustrated to be of the type shown previously in FIG. 4. A linear opening 358 in the external reflective enclosure 354 allows light to pass from the linear illumination source 370 to the lens 366. In order to achieve higher output irradiance and radiance for the linear illumination system, preferably linear opening 358 has a maximum width 364 that is less than the maximum inside width 362 of the external reflective enclosure 354. More preferably, the maximum width 364 of the linear opening 358 ranges from about 3% to about 75% of the maximum inside width 362 of the external reflective enclosure. Most preferably, the maximum width 364 of linear opening 358 ranges from about 5% to about 50% of the maximum inside width 362 of the external reflective enclosure. In addition, if linear light source 352 is a tubular fluorescent lamp, preferably the maximum width 364 of the linear opening 358 ranges from about 5% to about 100% of the width 360 of the linear light source 352. More preferably, the width 364 of the linear opening 358 ranges from about 20% to about 90% of the width 360 of the linear light source. Examples of lens 366 include, but are not limited to, a lenticular lens, an aspherical lenticular lens, a cylindrical rod lens, a plano-convex lenticular lens, a double-convex lenticular lens, a lenticular Fresnel lens, and multi-element lenses of any type. Especially useful are linear illumination systems in which the lens 366 is a cylindrical rod lens as is illustrated in FIGS. 10 and 11. Lens 366 may be constructed from any transparent material. Linear illumination systems may be used in many applications including, for example, optical scanners, facsimile machines, and photocopiers.

Figure 12:
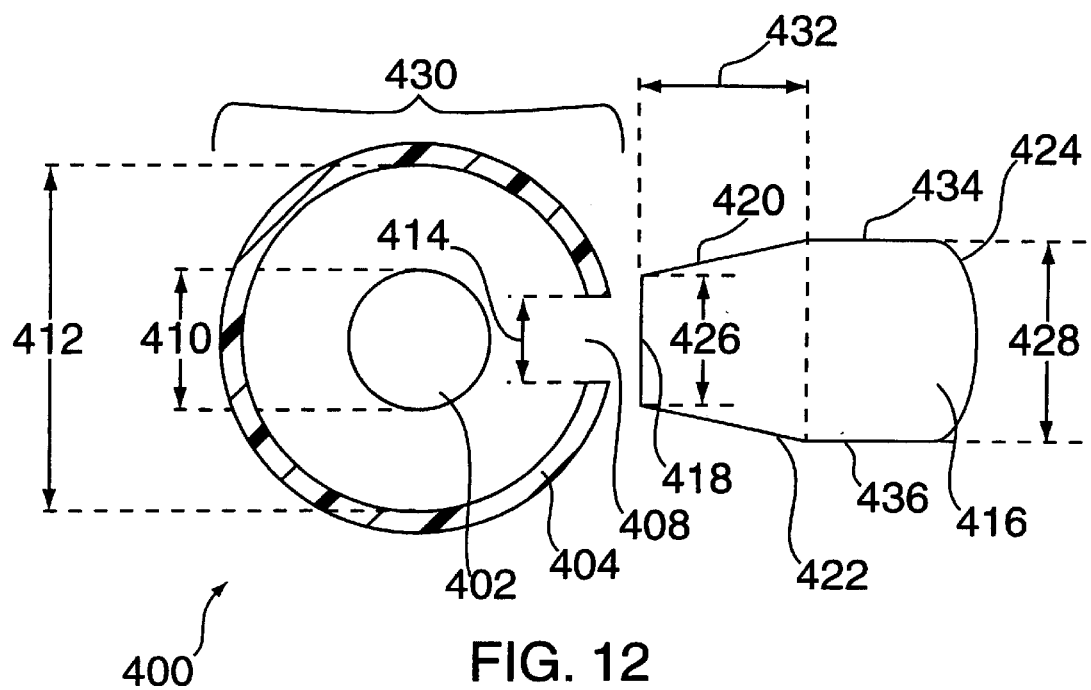
FIG. 12 is a schematic cross-sectional diagram of a linear illumination system utilizing the linear illumination source of FIG. 4 and a lens that functions both by refraction and total internal reflection.

FIG. 12 illustrates another embodiment of this invention. Linear illumination system 400 is comprised of linear illumination source 430 and a transparent optical element 416. By way of example, the linear illumination source 430 is illustrated to be of the type shown in FIG. 4 and is, in turn, comprised of linear light source 402 and external reflective enclosure 404. External reflective enclosure 404 has a linear opening 408 with a maximum width 414 that allows light to pass from the linear illumination source 430 to the transparent optical element 416. Transparent optical element 416 has an input surface 418 adjacent to opening 408, a tapered section of length 432 bounded by sidewalls 420 and 422, and an output surface 424. Optionally, transparent optical element 416 also includes a straight section with parallel sidewalls 434 and 436, whereby the straight section is positioned between the tapered section (bounded by the sidewalls 420 and 422) and the output surface 424. Preferably the input surface 418 is planar but planarity is not required. The output width 428 of the optical element 416 is preferably greater than the input width 426 of the tapered section. More preferably, the output width 428 of the optical element 416 is at least two times the input width 426. The sidewalls 420 and 422 of the tapered section may be planar, curved, or faceted. The output surface 424 of the transparent optical element 416 may also be planar, curved, or faceted. Preferably the output surface 424 is a curved lenticular lens, whereby the lens may have a single radius of curvature, may be parabolic in shape, or may have some general shape having no single radius of curvature. More preferably, output surface 424 has a single radius of curvature R, where the radius of curvature R may range from one-half of the output width 428 to about 1.5 times one-half of the output width 428. In other words, the range of the radius of curvature R is (width 428)/2 ≦ R ≦ (1.5)(width 428)/2.

Light enters transparent optical element 416 through input surface 418. Some of the light undergoes reflections from the inner surfaces of sidewalls 420 and 422 and from the inner surfaces of the optional sidewalls 434 and 436. The reflections may occur by TIR if the sidewalls 420, 422, 434, and 436 are uncoated or may occur by normal reflection if the sidewalls are coated with a reflective coating. Since the sidewalls 420 and 422 form an expanding taper, the light will be partially collimated by the tapered section of the optical element 416. The light then exits through the output surface 424 which can further shape the output light beam. Output surface 424 may result in a light output beam that is either more collimated or more focused.

Figure 13:
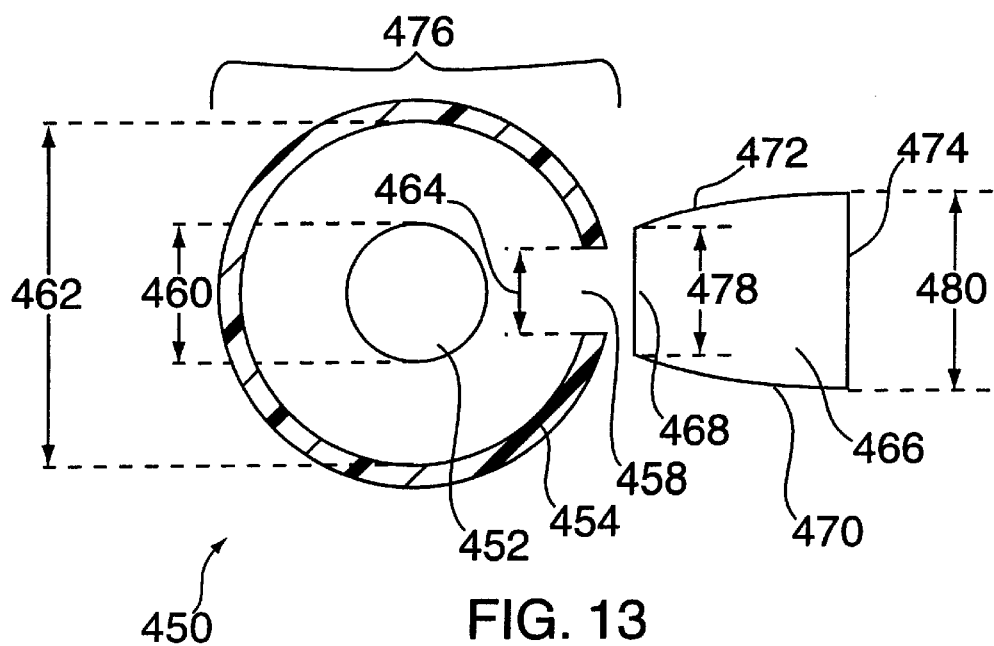
FIG. 13 is a schematic cross-sectional diagram of a linear illumination system utilizing the linear illumination source of FIG. 4 and a compound parabolic concentrator (CPC)

FIG. 13 illustrates another embodiment of this invention. Linear illumination system 450 is comprised of an illumination source 476 and a tapered optical structure 466. By way of example, linear illumination source 476 is illustrated to be of the type shown in FIG. 4. The illumination source 476 is further comprised of a linear light source 452 and an external reflective enclosure 454. An opening 458 in the external reflective enclosure 454 allows light to pass from the illumination source 452 to the tapered optical structure 466 having sidewalls 470 and 472. If the tapered optical structure 466 is a solid structure (not hollow), preferably the light input end 468 of tapered optical structure 466 is a planar surface, but planarity is not required. The output width 480 of tapered optical structure 466 is greater than the input width 478. Preferably, the output width 480 of the tapered optical structure 466 is at least two times the input width 478. Especially useful are linear illumination systems in which the sidewalls 470 and 472 of the tapered optical waveguide have a parabolic shape or the shape of a compound parabolic concentrator (CPC). The tapered optical structure 466 may be constructed from a solid transparent material having surfaces 470 and 472 that are either uncoated or coated with a reflective material or the tapered optical structure 466 may be a hollow structure with surfaces 470 and 472 coated with a reflective material and with open ends 468 and 474. Light enters the tapered optical structure 466 at input end 468, reflects from surfaces 470 and 472 and exits at output end 474. As a result of the tapered sides of the optical structure 466, the light at the output end 474 of the taper is more collimated than the light at the input end 468. In the case that the optical structure 466 is fabricated from a clear dielectric material, it is also possible to make the output end 474 not planar as shown but convex. In such a case, a given degree of collimation can be achieved with an element of shorter length, where length is defined as the perpendicular distance from input end 468 to the output end 474.

Figure 14:
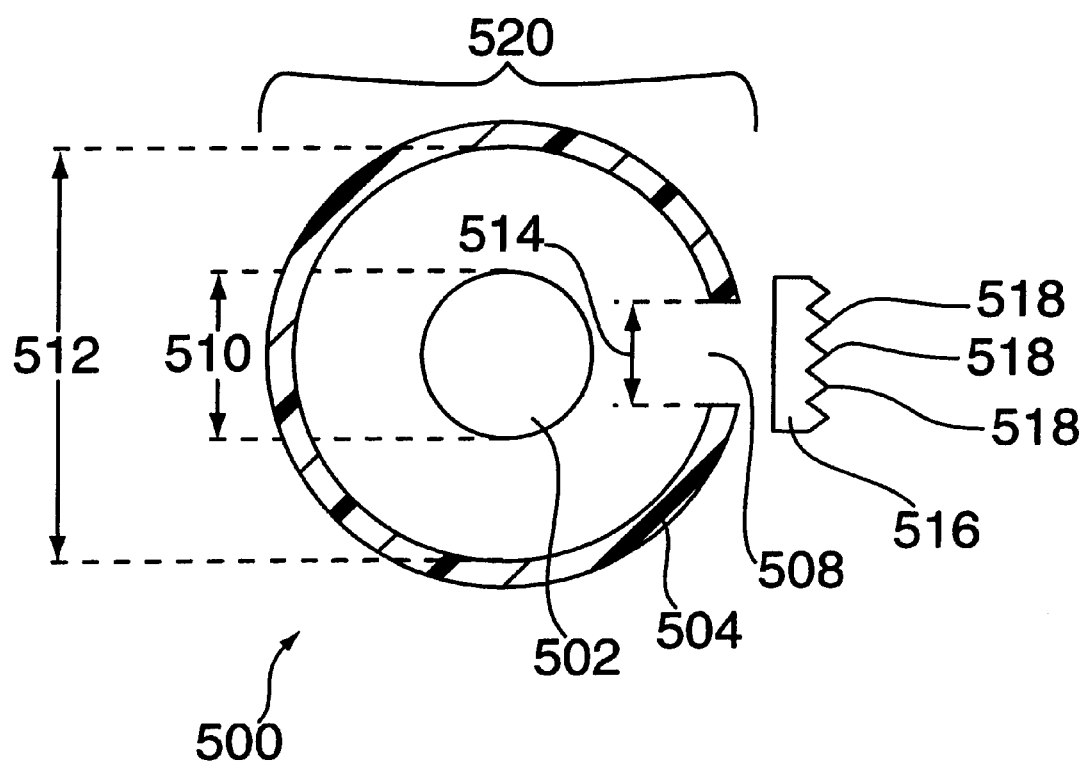
FIG. 14 is a schematic cross-sectional diagram of a linear illumination system utilizing the linear illumination source of FIG. 4 and an array of optical elements.

Another embodiment of this invention is illustrated in FIG. 14 as linear illumination system 500. Linear illumination system 500 is comprised of linear illumination source 520 and an array 516 of lenticular optical elements 518. By way of example, linear illumination source 520 is illustrated to be of the type shown in FIG. 4. Linear illumination source 520 is further comprised of linear light source 502 which is partially surrounded by external reflective enclosure 504 with opening 508. The lenticular optical elements 518 may include lenticular prisms and lenticular lenses used separately or in combination. If the lenticular optical elements 518 are lenticular prisms, the sidewalls of the prisms may be planar, curved or faceted. If the lenticular optical elements 518 are lenticular lenses, the lenses may have one radius of curvature, multiple radii of curvature, or may be aspherical lenticular lenses. The purpose of the array 516 of lenticular optical elements is to further shape or collimate or focus the light emerging from opening 508.

The following examples are included to illustrate some embodiments of this invention but are not meant to limit the scope of the invention.

EXAMPLE 1

This example illustrates forming a reflector using a combination of a layer of diffuse reflective material and a layer of specular reflective material. Reflectivity measurements were done using a commercially available Macbeth #3100 Spectrophotometer. The reflectivity of a 0.5 mm (0.020 inch) thick sheet of white, diffuse, polytetrafluoroethylene material (product number 128-10 white) produced by Furon, Hoosick Falls, N.Y., was measured and found to be 95.6% with no specular reflector backing. When a specular reflective sheet of Silverlux™ (3M) having a reflectance of 92% was placed on the back side of the white diffuse material, the reflectivity of the composite material increased to 96.8%, a number that is larger than either of the two reflective sheets measured separately. Increases in reflectivity of this magnitude are quite important for illumination systems in which light is reflected many times inside the system. For example, if light is reflected twenty times inside the illumination system, the overall efficiency of the twenty reflections would be $(0.956)^{20}$ or 40.7% for the diffuse reflective material used alone, $(0.920)^{20}$ or 18.9% for the specular reflective material used alone, and $(0.968)^{20}$ or 52.2% for the combination of reflective materials. In this example, the combination of diffuse and specular reflective materials is 28% more efficient than the diffuse reflective material used alone and 176% more efficient than the specular reflective material used alone.

EXAMPLE 2

Figure 1:
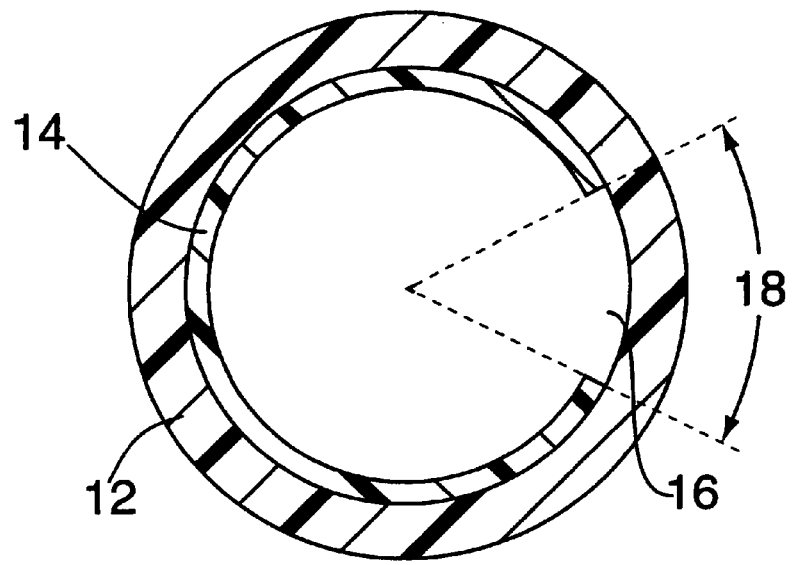
FIG. 1 is a schematic cross-sectional diagram of an internal aperture lamp of the prior art.
Figure 2:
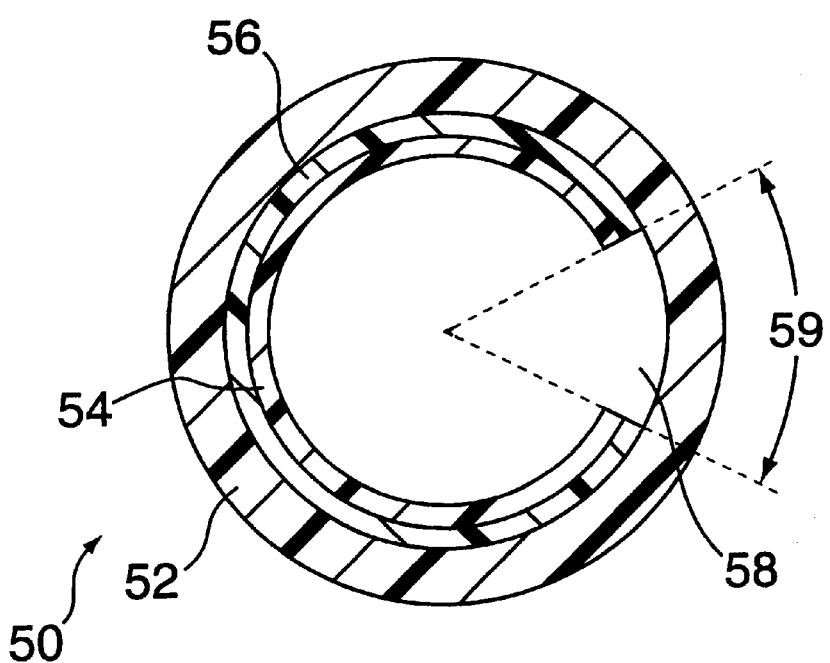
FIG. 2 is a schematic cross-sectional diagram of an alternative internal aperture lamp of the prior art.

In this example, the efficiency of a commercially available fluorescent aperture lamp having an internal aperture (utilizing the prior art configuration shown schematically in FIG. 2) was compared to an improved illumination source design as described in this invention.

The commercially available internal aperture lamp was a 3 mm diameter cold-cathode fluorescent lamp made by LCD Lighting. This lamp had a 90° internal aperture which allowed light to escape predominantly from one side of the lamp. Note that a 90° aperture corresponds to the case where the width of the aperture is approximately 50% of the internal width of the reflecting layer. The lamp was placed inside an integrating sphere and the total light output was measured. Dividing the total light output by the length of the lamp resulted in an output per unit length of 4.0 lumens/inch.

A second lamp (the same length as the preceding aperture lamp) was obtained from LCD Lighting having no internal aperture but having the same technical characteristics (3 mm diameter and the same phosphor and gas fill compositions) as the preceding aperture lamp. This lamp was tightly wrapped with a combination of diffuse and specular reflective materials except for a linear opening of 90° which allowed the light to escape. In this case, the combination of diffuse and specular reflective materials was on the outside of the glass envelope of the lamp forming a linear external opening. The combination of diffuse and specular reflective materials was made up of a 0.25 mm (0.010 inch) thick sheet of Furon™, a polytetrafluoroethylene diffuse reflective material purchased from Fluorglas, and was backed by a layer of Silverlux™ specular reflective material purchased from 3M. The reflecting materials were held in place by completely surrounding the lamp and the reflective materials with a transparent plastic shrink tube and then heating the shrink tube until it tightly compressed the reflecting materials onto the outside surface of the lamp. The illumination source was placed inside an integrating sphere and the total light output was measured. Dividing by the length of the lamp to convert to lumens/inch resulted in an output of 6.8 lumens/inch which is a 70% improvement in efficiency over the internal aperture lamp.

EXAMPLE 3

The two illumination sources of Example 2, the internal 90° aperture lamp from LCD Lighting and the improved linear illumination source of this invention, were each used to illuminate a surface 4 mm from the lamps. The irradiance (in units of mW/cm$^2$) was measured for both sources. At the 4 mm distance, the irradiance from the standard internal aperture lamp was 3.4 mW/cm$^2$. The irradiance from the improved illumination source of this invention was 5.6 mW/cm$^2$, an improvement of 65%.

EXAMPLE 4

Figure 15:
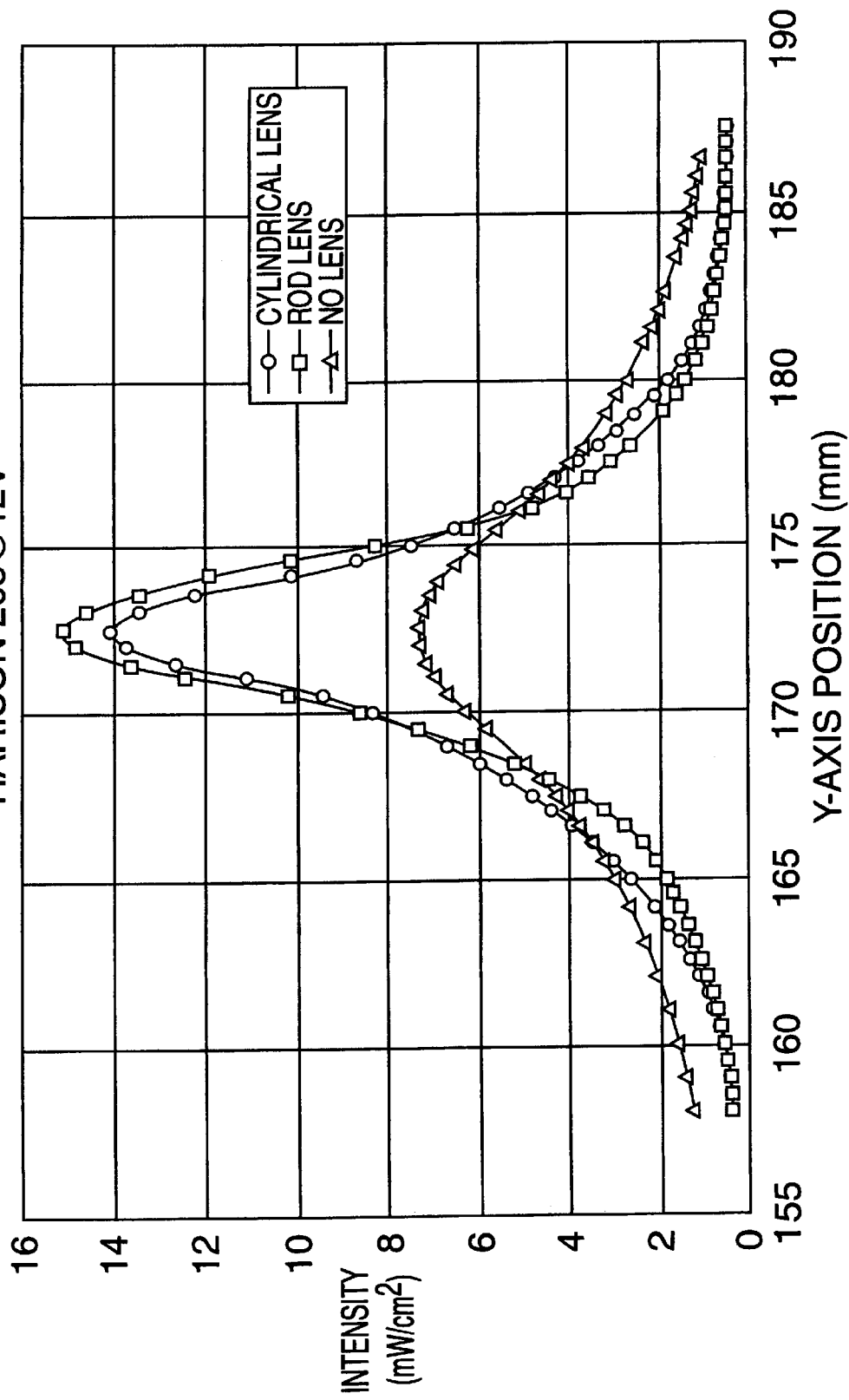
FIG. 15 is a plot of intensity (irradiance) versus detector position.

A linear illumination source was constructed utilizing the configuration shown schematically in FIG. 4 and was compared to a linear illumination system that was constructed utilizing the configuration shown schematically in FIG. 10 and that includes an external lens. For both cases, the light source was a cold-cathode fluorescent lamp made by Harrison that had an outside diameter of 2.6 mm and a length of 268 mm. The lamp was driven by an inverter using an inverter input power of approximately 3.7 watts. The light output of the bare lamp was measured using a calibrated integrating sphere and found to be 123 lumens. A external reflective enclosure surrounded the lamp except for a linear opening whose width could be adjusted. The external reflective enclosure was constructed from two pieces of Spectralon™ (from Labsphere Inc.). Spectralon™ is a diffuse reflecting solid whose reflectivity depends on the thickness of the material. For 555 nm light, a section of Spectralon™ that is 3 mm thick has a reflectivity of 97.2%. The two pieces of reflecting material were machined such that the shape of the enclosure was oval. The maximum inside width of the oval enclosure was approximately 7.0 mm and a minimum inside width of the oval enclosure was approximately 4.6 mm. A linear opening in one side of the enclosure was adjusted to have a uniform width of 1.15 mm. Note that when the width of the linear opening was 1.15 mm, the opening width is only approximately 16% of the maximum internal width of the enclosure and approximately 44% of the width of the lamp. For the case of the linear illumination system, either a rod lens approximately 3.18 mm in diameter or a plano-convex cylinder lens was placed outside the enclosure and approximately 3.5 mm from the oval cavity in the external reflective enclosure. For all three cases (i.e. no lens, a rod lens, or a plano-convex cylinder lens), the irradiance (in mW/cm$^2$) of the linear illumination system was measured at a distance of 7 mm from the rod lens using a 1 mm diameter detector. Within the 7 mm distance was a 3 mm thick glass plate which simulated the optical arrangement typically encountered inside a flatbed document scanner. The detector was moved from side to side over a range of approximately 30 mm to map out the shape of the irradiance distribution perpendicular to the long axis of the linear illumination system. The results are shown in FIG. 15. For the linear illumination source with no lens, the resulting peak irradiance was approximately 7.3 mW/cm$^2$. Placing a plano-convex cylinder lens at the linear opening of the illumination source increased the peak irradiance to approximately 14 mW/cm$^2$. Replacing the cylinder lens with a rod lens resulted in a peak irradiance of approximately 15 mW/cm$^2$. Utilizing the lens, whether a rod lens or a plano-convex cylinder lens, greatly improved the peak irradiance.

EXAMPLE 5

Figure 16:
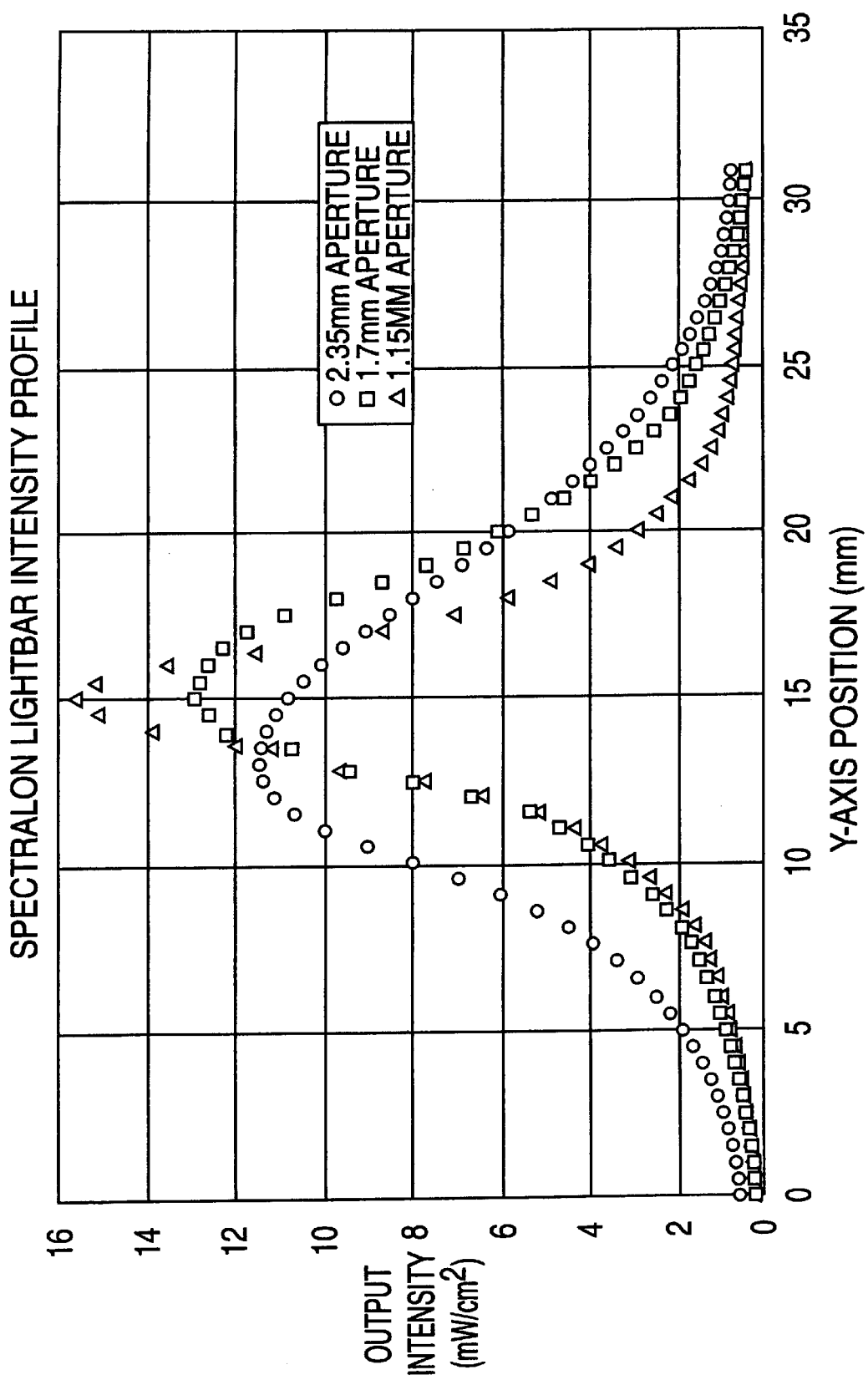
FIG. 16 is a plot of intensity (irradiance) versus detector position.
Figure 17:
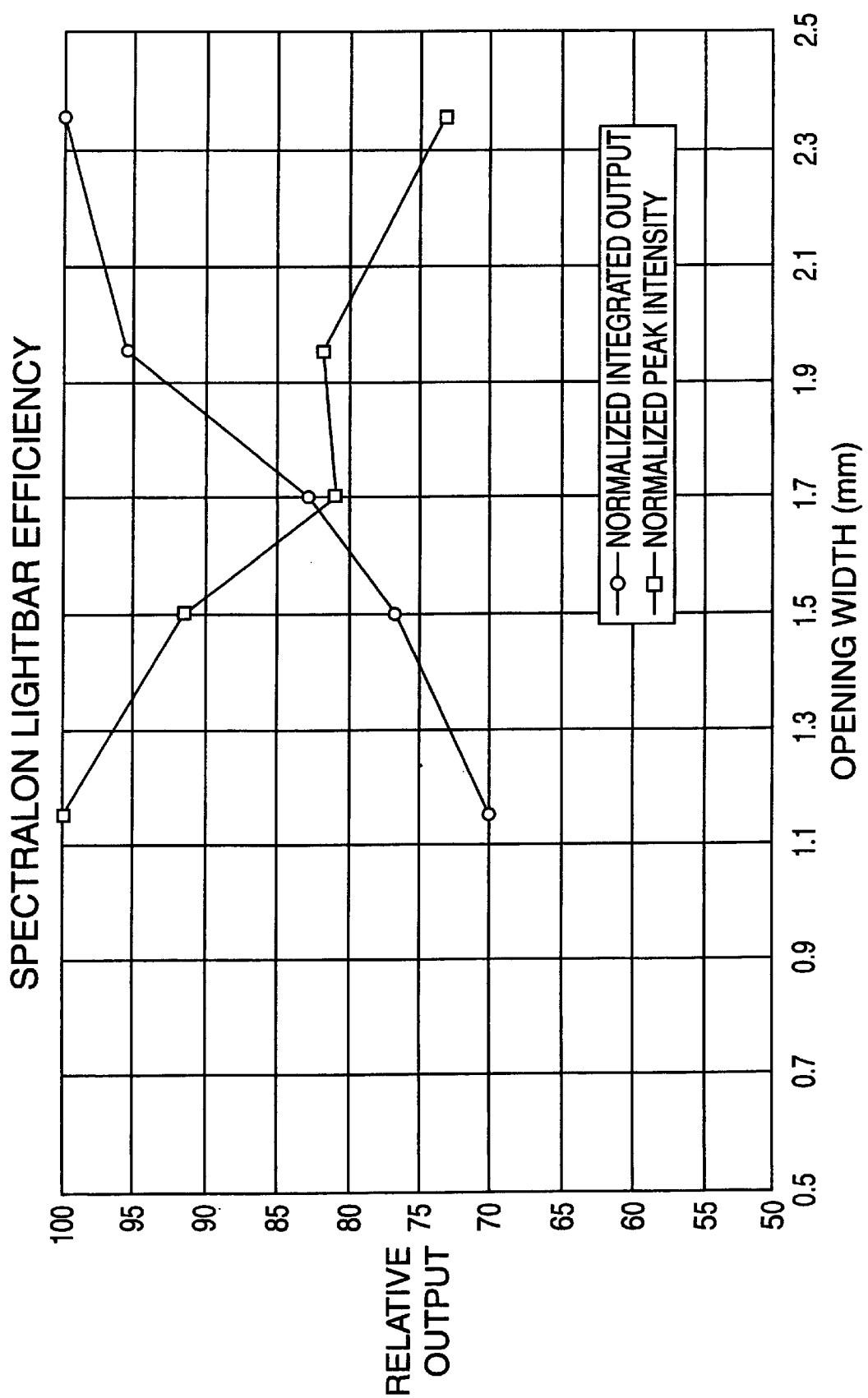
FIG. 17 is a plot of relative output versus opening width.

A linear illumination system was constructed utilizing the configuration shown schematically in FIG. 10 and included a light source, an external reflective enclosure, and an external lens. The light source was a cold-cathode fluorescent lamp made by Harrison that had an outside diameter of 2.6 mm and a length of 268 mm. The lamp was driven by an inverter using an inverter input power of approximately 3.7 watts. The light output of the bare lamp was measured using a calibrated integrating sphere and found to be 123 lumens. A external reflective enclosure surrounded the lamp except for a linear slit whose width could be adjusted. The external reflective enclosure was constructed from two pieces of Spectralon™ (from Labsphere Inc.). Spectralon™ is a diffuse reflecting solid whose reflectivity depends on the thickness of the material. For 555 nm light, a section of Spectralon™ that is 3 mm thick has a reflectivity of 97.2%. The two pieces of reflecting material were machined such that the shape of the enclosure was oval. The maximum inside width of the oval enclosure was approximately 7.0 mm and a minimum inside width of the oval enclosure was approximately 4.6 mm. A linear opening in one side of the enclosure could be adjusted to have a uniform width ranging from 1.15 mm to 2.35 mm. Note that when the width of the linear opening is 2.35 mm, the opening width is less than the width (2.6 mm) of the fluorescent lamp and only approximately 35% of the maximum inside width of the enclosure. When the width of the linear opening is 1.15 mm, the opening width is only approximately 16% of the maximum internal width of the enclosure and approximately 44% of the width of the lamp. A cylindrical rod lens approximately 3.18 mm in diameter was placed outside the enclosure and approximately 3.5 mm from the oval cavity in the external reflective enclosure. The irradiance (in mW/cm$^2$) of the linear illumination system was measured at a distance of 7 mm from the rod lens using a 1 mm diameter detector. Within the 7 mm distance was a 3 mm thick glass plate which simulated the optical arrangement typically encountered inside a flatbed document scanner. The detector was moved from side to side over a range of approximately 30 mm to map out the shape of the irradiance distribution perpendicular to the long axis of the linear illumination system. The results are shown in FIG. 16. The narrowest opening width, 1.15 mm, had the highest peak irradiance (approximately 16 mW/cm$^2$) but also the narrowest irradiance distribution (a full width at half maximum of approximately 5 mm). In contrast, the widest opening width (2.35 mm) had the lowest peak irradiance (approximately 11.5 mW/cm$^2$) and the widest irradiance distribution (a full width at half maximum of approximately 11 mm). For both the narrowest and widest opening widths measured, the peak values of irradiance are much higher than the irradiance of the same linear illumination source without the lens. The total integrated light output from the linear illumination system is directly related to the opening width and is highest for the widest opening as shown in FIG. 17. The normalized peak irradiance is inversely related to the opening width and is highest for the smallest opening width (also shown in FIG. 17).

EXAMPLE 6

An experiment was done to measure the output efficiency of a linear illumination source as a function of the percent reflectivity of the reflective material. A linear illumination source was constructed that included a linear light source, an external tubular enclosure and a layer of reflective material that lined the inside surface of the external tubular enclosure except for a linear opening having a fixed width of 1.5 mm. The linear light source was a cold-cathode fluorescent lamp that had a diameter of 2.6 mm and a length of 268 mm. The lamp was driven by an inverter using an inverter input power of approximately 3.7 watts. The external enclosure was constructed from an acrylic tube that had an inside diameter of 6.4 mm. Five different reflective materials were placed sequentially inside the enclosure. The materials were: polyethersulfone filter material (obtained from Pall Gelman Sciences), Spectraflect™ (obtained from Labsphere), Duraflect™ (obtained from Labsphere), Silverlux™ (obtained from 3M), and Predator™ (obtained from Pall Gelman Sciences). All the reflecting materials with the exception of Silverlux™ were diffuse reflectors. The table below shows the resulting illumination source efficiencies as a function of the material reflectivity.

| Reflecting Material | Reflectivity | Efficiency |
| --- | --- | --- |
| Polyethersulfone | 97.7% | 54.3% |
| Spectraflect ™ | 97.5% | 54.3% |
| Duraflect ™ | 96% | 48% |
| Silverlux ™ | 92% | 41.9% |
| Predator ™ | 85% | 31.3% |

Thus, the table demonstrates that small changes in the reflectivity can result in large changes in the efficiency of the linear illumination source.

EXAMPLE 7

Figure 18:
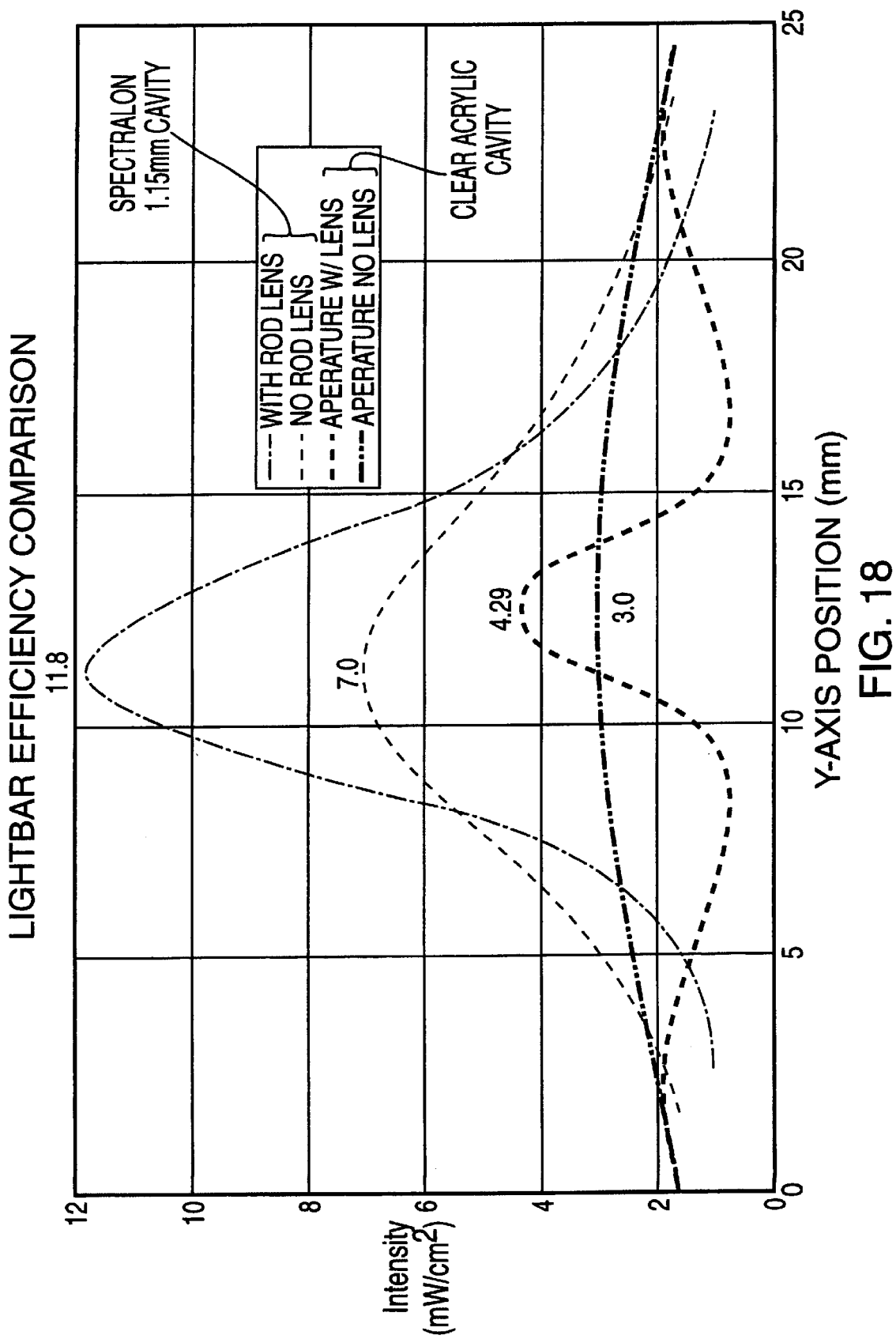
FIG. 18 is a plot of intensity (irradiance) versus detector position.

In this example, two illumination devices utilizing an aperture lamp were compared to two improved illumination devices as taught by this invention. Device 1 was a commercially available 3 mm diameter cold-cathode aperture fluorescent lamp made by LCD Lighting. This lamp had a 90° internal aperture which allowed light to escape predominantly from one side of the lamp. Note that a 90° aperture corresponds to the case where the width of the aperture is approximately 50% of the internal width of the reflecting layer. Device 2 used the same aperture lamp as Device 1 but added a 3.18 mm diameter rod lens placed approximately 3.5 mm from the lamp aperture. For both device 1 and device 2, the lamp was placed inside a clear acrylic enclosure but no reflective material was used for the enclosure. Devices 3 and 4 are examples of embodiments of this invention. Devices 3 and 4 utilized a second lamp obtained from LCD Lighting having no internal aperture but having the same technical characteristics (3 mm diameter and the same phosphor and gas fill compositions) as the preceding aperture lamp. In addition, for devices 3 and 4, an external reflective enclosure was placed around the lamp where the external reflective enclosure had a linear opening whose width was adjusted to 1.15 mm. The external reflective enclosure was constructed from two pieces of Spectralon™ (from Labsphere Inc.). Spectralon™ is a diffuse reflecting solid whose reflectivity depends on the thickness of the material. For 555 nm light, a section of Spectralon™ that is 3 mm thick has a reflectivity of 97.2%. The two pieces of reflecting material were machined such that the shape of the enclosure was oval. The maximum inside width of the oval enclosure was approximately 7.0 mm and a minimum inside width of the oval enclosure was approximately 4.6 mm. For device 4, a rod lens approximately 3.18 mm in diameter was placed approximately 3.5 mm from the oval cavity in the external reflective enclosure. Device 3 had no lens. The irradiance (in mW/cm$^2$) of the linear illumination system was measured at a distance of 7 mm from the rod lens using a 1 mm diameter detector. Within the 7 mm distance was a 3 mm thick glass plate which simulated the optical arrangement typically encountered inside a flatbed document scanner. The detector was moved from side to side over a range of approximately 30 mm to map out the shape of the irradiance distribution perpendicular to the long axis of the linear illumination system. The results are shown in FIG. 18. Device 1 (the aperture lamp alone) had the worst peak irradiance of about 3.0 mW/cm$^2$. For device 2 (the aperture lamp plus the rod lens), the peak irradiance increased only slightly to 4.29 mW/cm$^2$. Device 3 (the non-aperture lamp used with a reflective enclosure taught by this invention) had a much improved peak irradiance of 7.0 mW/cm. Device 4 (the non-aperture lamp used with a reflective enclosure and rod lens arrangement taught by this invention) had the highest peak irradiance of 11.8 mW/cm$^2$. These results indicated that a non-aperture lamp used with an external reflecting enclosure having a narrow linear opening gave a higher directed irradiance than an internal aperture lamp and that even further improvement in the directed irradiance was obtained by adding an additional optical element (in this case, a rod lens).

It should be understood that this invention is applicable to a wide variety of devices requiring linear illumination sources and linear illumination systems. Examples include, but are not limited to: scanners, facsimile machines, photocopiers and direct illumination devices for commercial, office, residential, outdoor, automotive, and appliance applications. The inventions herein may also be applied to displays (e.g. flat panel displays) for computer, automotive, military, aerospace, consumer, commercial, and industrial applications.

While there has been described what is believed to be the preferred embodiments of the invention, those skilled in the art will recognize that other and further modifications may be made thereto without departing from the spirit of the invention, and it is intended to claim all such embodiments that fall within the true scope of the invention.

We claim:

1. A linear illumination source comprising:
   (a) a linear light source having a width $w_1$ in a direction perpendicular to the long axis of the linear light source; and
   (b) an external reflective enclosure partially surrounding the linear light source, wherein the external reflective enclosure has a maximum inside width $w_2$, and wherein the external reflective enclosure has at least one linear opening of maximum width $w_3$ such that $(0.03)(w_2) \leq w_3 \leq (0.75)(w_2)$ wherein the external reflective enclosure comprises an engineering thermoplastic filled with fine particles of a clear or white filler wherein the index of refraction of said fine particles is greater than the index of refraction of said thermoplastic; and wherein the enclosure comprises a reflecting material having a reflectivity R greater than or equal to 95%.

2. The linear illumination source of claim 1, wherein said linear light source is a tubular fluorescent lamp.

3. The linear illumination source of claim 2, wherein $(0.1)(w_1) \leq w_3 \leq w_1$.

4. The linear illumination source of claim 2, wherein $(0.2)(w_1) \leq w_3 \leq (0.9)(w_1)$.

5. The linear illumination source of claim 1, wherein said linear light source is an array of light emitting diodes, an array of laser diodes, at least one organic light emitting diode, or at least one electroluminescent strip.

6. The linear light source of claim 5, wherein the linear light source is comprised of light emitters of more than one color.

7. The linear illumination source of claim 1, wherein the reflective material of said external reflective enclosure has a reflectivity $R \geq 90\%$.

8. The reflective material of claim 1, wherein the reflective material of said external reflective enclosure is either a diffuse reflector, a specular reflector, or a combination of diffuse and specular reflectors.

9. The linear illumination source of claim 1, wherein said linear opening has a maximum width $w_3$, such that $(0.05)(w_2) \leq w_3 \leq (0.50)(w_2)$.

10. The linear illumination system of claim 1 wherein the external reflective enclosure has a circular cross sectional shape.

11. The linear illumination system of claim 1 wherein the external reflective enclosure comprises a structural support.

12. The linear illumination source comprising:
(a) a linear light source having a width $w_1$ in a direction perpendicular to the long axis of the linear light source; and
(b) an external reflective enclosure partially surrounding the linear light source, wherein the external reflective enclosure has a maximum inside width $w_2$, and wherein the external reflective enclosure has at least one linear opening of maximum width $w_3$ such that $(0.03)(w_2) \leq w_3 \leq (0.75)(w_2)$, and wherein said linear opening has a width that varies along the length of the illumination source.

13. The linear illumination source of claim 12, wherein said linear light source is a tubular fluorescent lamp.

14. The linear illumination source of claim 12, wherein $(0.1)(w_1) \leq w_3 \leq w_1$.

15. The linear illumination source of claim 12, wherein $(0.2)(w_1) \leq w_3 \leq (0.9)(w_1)$.

16. The linear illumination source of claim 12, wherein said linear light source comprises an array of light emitting diodes, an array of laser diodes, at least one organic light emitting diode, or at least one electroluminescent strip.

17. The linear illumination source of claim 12, wherein the linear light source is comprised of light emitters of more than one color.

18. The linear illumination source of claim 12, wherein the reflective material of said external reflective enclosure has a reflectively $R \geq 90\%$.

19. The linear illumination source of claim 12, wherein said external reflective enclosure comprises a reflective material having a reflectively $R \geq 95\%$.

20. The linear illumination source of claim 12, wherein the reflective material of said external reflective enclosure is either a diffuse reflector, a specular reflectors or a combination of diffuse and specular reflectors.

21. The linear illumination source of claim 12, comprising an engineering thermoplastic filled with fine particles of a clear or white filler wherein the index of refraction of said line particles is greater than the index of refraction of said thermoplastic.

22. The linear illumination source of claim 12, wherein said linear opening has a width that varies along the length of the illumination source.

23. The linear illumination source of claim 12, wherein said linear opening has a maximum with $w_3$, such that $(0.05)(w_2) \leq w_3 \leq (0.05)(w_2)$.

* * * * *